United States Patent [19]
Blom

[11] Patent Number: 4,773,412
[45] Date of Patent: Sep. 27, 1988

[54] SPEAKING TRACHEOSTOMY TUBE

[75] Inventor: Eric D. Blom, Indianapolis, Ind.

[73] Assignee: Hansa Medical Products, Inc., Indianapolis, Ind.

[21] Appl. No.: 900,078

[22] Filed: Aug. 25, 1986

[51] Int. Cl.⁴ .......................................... A61M 16/00
[52] U.S. Cl. .................................. 128/207.14; 623/9
[58] Field of Search .................... 128/201.19, 207.14, 128/207.15, 207.16, 207.17, 200.26, 205.13, 205.15, 205.16, 205.17, 205.24; 623/9; 381/70

[56] References Cited

U.S. PATENT DOCUMENTS

| 2,273,077 | 2/1942 | Wright | 623/9 |
|---|---|---|---|
| 3,557,785 | 1/1971 | McQueen | 128/205.16 |
| 4,318,399 | 3/1982 | Berndtsson | 128/205.24 |
| 4,327,721 | 5/1982 | Goldin et al. | 128/207.15 |
| 4,489,440 | 12/1984 | Chaoni | 623/9 |
| 4,586,931 | 5/1986 | Blom et al. | 623/9 |
| 4,612,664 | 9/1986 | Walsh et al. | 623/9 |
| 4,633,864 | 1/1987 | Walsh | 128/207.15 |

FOREIGN PATENT DOCUMENTS

| 1136544 | 12/1956 | France | 128/205.17 |
|---|---|---|---|
| 1248230 | 8/1967 | Fed. Rep. of Germany . | |

OTHER PUBLICATIONS

"Clinicopathological Conference ", British Medical Journal, Aug. 27, 1967, p. 547.
"Acetylcysteine and Speaking Tracheostomy Tubes," Journal of the American Medical Association, Oct. 16, 1981, vol. 246, No. 16, p. 1771.
"Speaking Cuffed Tracheostomy Tube," Safar, Peter, MD and Ake Grenvik, MD, Critical Care Medicine, vol. 3, No. 1, Jan.-Feb. 1975, pp. 23-26.

Primary Examiner—Edward M. Coven
Assistant Examiner—J. P. Lacyk
Attorney, Agent, or Firm—Barnes & Thornburg

[57] ABSTRACT

This invention relates to tracheostomy tubes and particularly to a tracheostomy tube construction and a system incorporating a talking tracheostomy tube. A pneumatic vibrator is provided for generating sonic vibrations. A tracheostomy tube includes a main airway and secondary airway. The secondary airway extends generally along the main airway for a substantial portion of its length. Furthermore there is an entryway to the secondary airway outside the entrance of the tracheostomy tube into a tracheostomy. And an exit from the secondary airway adjacent its end remote from the entryway. A source of compressed air is coupled to the pneumatic vibrator and the pneumatic vibrator coupled to the entryway to supply air containing sonic vibrations to permit the wearer of the tracheostomy tube to articulate audibly comprehensible speech.

6 Claims, 1 Drawing Sheet

U.S. Patent  Sep. 27, 1988  4,773,412
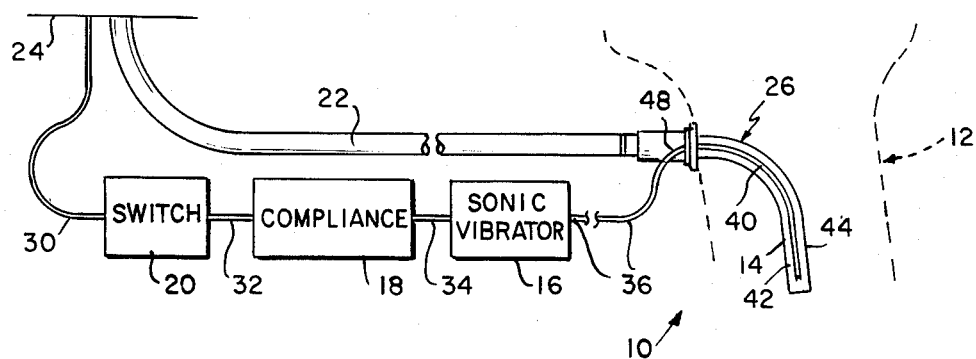
FIG. 1
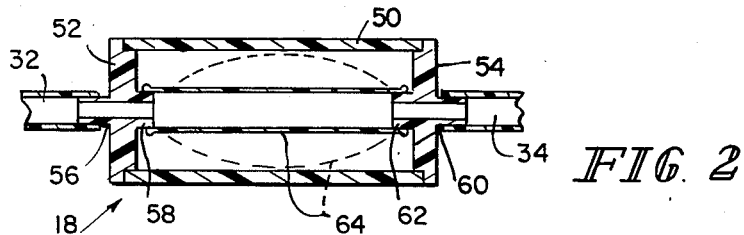
FIG. 2
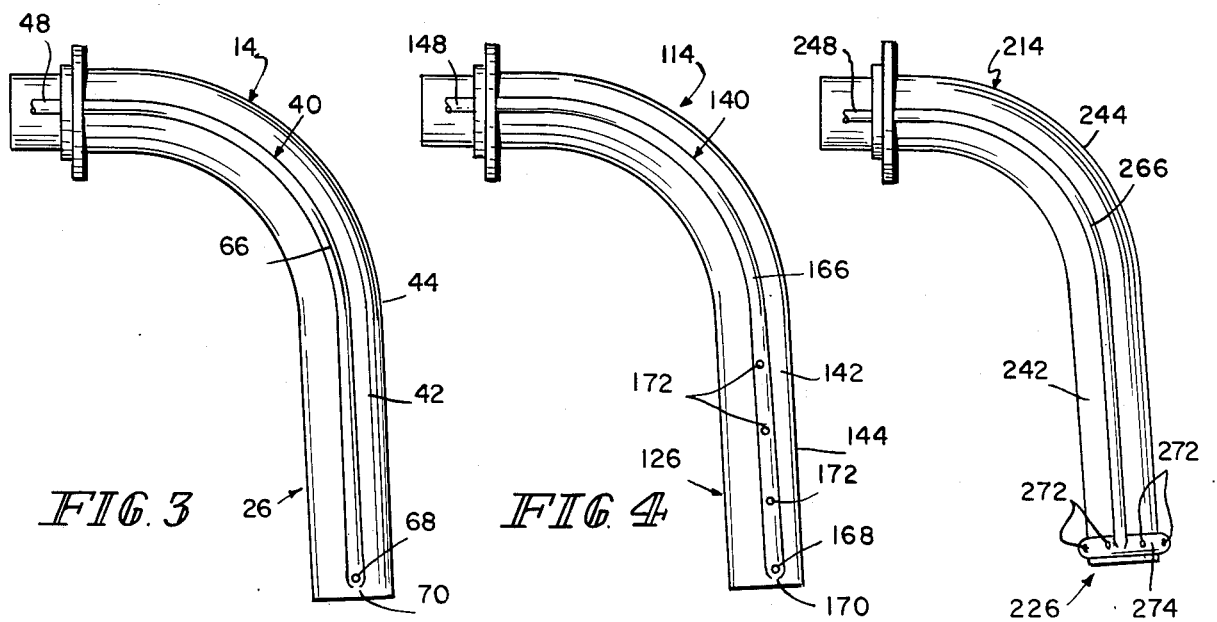
FIG. 3
FIG. 4
FIG. 5
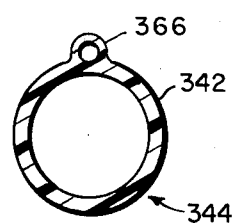
FIG. 6
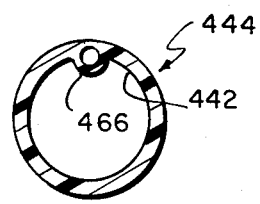
FIG. 7

SPEAKING TRACHEOSTOMY TUBE

This invention relates to tracheostomy tubes and particularly to a tracheostomy tube construction and a system incorporating a talking tracheostomy tube.

Talking tracheostomy tubes are known. An example would be the so-called "Pitt speaking tracheostomy tube" available from National Catheter Corporation. On these types of tubes, in addition to the conventional tracheostomy airway, a secondary airway is provided by a smaller cross-section tube glued or otherwise attached to the main airway-providing tube. This secondary airway is normally coupled through a switch and a pressure regulator to a source of compressed air, such as hospital air at 50–60 pounds per square inch. The end of the secondary airway which lies within the trachea of the user is positioned fairly close to, and generally below, the vocal cords of the user. When the user wishes to speak, the user operates the switch which permits compressed air to flow from the end of the secondary airway. Theoretically, this should cause the vocal cords of the wearer to vibrate, permitting the wearer to articulate audibly comprehensible speech. However, a number of problems arise which hamper this process. Even though the air is delivered to the throat of the wearer, typically below the vocal cords, as the air escapes upward through the larynx it frequently does not cause sufficient vibrations of the vocal cords for the sound to be heard. One cause of this is believed to be related to the fact that bypassing the upper limb of the airway by surgical tracheotomy results in the vocal cords temporarily becoming inadequately approximated, so that when air is delivered between them, what frequently results is a whisper rather than an audible voice. The vocal cords must be closed against each other to produce audible voice. Another problem is that the opening in the secondary airway through which the compressed air escapes is frequently too close to the tracheostomy. This permits air which has been channeled down the secondary airway for speaking to escape through the tracheostomy. Little or no air passes upward through the vocal cords into the pharynx, and the only audible sound is turbulent air escaping around the tracheostomy tube.

According to one aspect of the invention a pneumatic vibrator is provided for generating sonic vibrations. A tracheostomy tube includes means for providing a main airway and means for providing a secondary airway. The secondary airway-providing means extends generally along the main airway-providing means for a substantial portion of its length. Means provide an entryway to the secondary airway outside the entrance of the tracheostomy tube into a tracheostomy. Means provide an exit from the secondary airway adjacent its end remote from the entryway. Means are provided for coupling a source of compressed air to the pneumatic vibrator and for coupling the pneumatic vibrator to the entryway to supply air containing sonic vibrations to permit the wearer of the tracheostomy tube to articulate audibly comprehensible speech.

Illustratively, the means for coupling the pneumatic vibrator to a source of compressed air comprises means providing a housing, an inlet extending through the wall of the housing to provide an inlet for compressed air into the housing, an outlet extending through the wall of the housing to provide an outlet for compressed air from the housing, and resilient elastic tubing extending between the inlet and outlet inside the housing to add compliance to the system for providing compressed air to the pneumatic vibrator. Illustratively, the resilient elastic tubing is balloon-like.

Additionally according to an illustrative embodiment of the invention, additional exits are provided through the wall of the secondary airway between the entryway and the first-mentioned exit from the secondary airway.

According to an illustrative embodiment, the means for providing an exit from the secondary airway adjacent its end remote from the entryway comprises means providing a passageway extending generally transversely to the longitudinal extent of the tracheostomy tube generally perimetrally around the means for providing the main airway, the transverse passageway being in open communication with the secondary airway, and means providing one or more openings through the wall of the transverse passageway to permit exit of air supplied to the entryway.

Further according to an illustrative embodiment, the transverse passageway extends completely around the perimeter of the means for providing the main airway.

According to another aspect of the invention, means are provided for generating sonic vibrations. A tracheostomy tube includes means for providing a main airway and means for providing a secondary airway. The secondary airway-providing means extends generally along the main airway-providing means for a substantial portion of its length. Means provide an entryway to the secondary airway outside the entrance of the tracheostomy tube into a tracheostomy. Means are provided for coupling the means for generating sonic vibrations to the entryway to supply sonic vibrations thereto. Means provide a passageway extending generally transversely of the longitudinal extent of the tracheostomy tube generally perimetrally around the sidewall of the means for providing the main airway and intersecting the means for providing the secondary airway. The transverse passageway and secondary airway are in open communication with each other, and an opening is provided in the wall of the transverse passageway so that sonic vibrations introduced into the entryway exit from the opening.

According to yet another aspect of the invention, a pneumatic vibrator generates sonic vibrations. Means are provided for introducing the sonic vibrations into the pharynx of a wearer. Means are provided for coupling the pneumatic vibrator to the means for introducing the sonic vibrations into the pharynx of the wearer. Means are provided for coupling the pneumatic vibrator to a source of compressed air, such means including a housing, means extending through a wall of the housing to provide an inlet for compressed air thereto, means extending through a wall of the housing to provide an outlet for compressed air therefrom, and means for providing a compliance, the compliance-providing means extending within the housing between the means providing the inlet to the housing and the means providing the outlet from the housing to add compliance to the system for providing compressed air to the pneumatic vibrator.

The invention may best be understood by referring to the following description and accompanying drawings which illustrate the invention. In the drawings:

FIG. 1 illustrates a schematic diagram of a system employing various aspects of the invention in a ventilation system for a patient;

FIG. 2 illustrates a longitudinal sectional side elevation view of a detail of the system of FIG. 1; and FIGS. 3–7 illustrate alternative constructions of a detail of the system of FIG. 1.

Referring now particularly to FIG. 1, a system 10 for ventilating a patient 12 includes a tracheostomy tube 14, a pneumatic vibrator 16 for providing sonic vibrations in a stream of compressed air being supplied to the tracheostomy tube 14, a compliance 18, and a switch 20. A length 22 of relatively larger inside diameter tubing couples a source 24 of compressed air, such as hospital compressed air regulated to a slightly higher pressure than atmospheric pressure, to the main airway 26 of the tracheostomy tube 14 to supply breathing air to the patient 12.

Additional lengths 30, 32, 34 and 36 of relatively smaller inside diameter tubing respectively couple a source of higher pressure (e.g., 50–60 p.s.i.) compressed air to switch 20, switch 20 to compliance 18, compliance 18 to pneumatic vibrator 16, and pneumatic vibrator 16 to a secondary airway 40 which extends generally parallel with the longitudinal extent of tracheostomy tube 14 along the sidewall 42 of a tube 44, the interior of which forms the main airway 26. Although not shown in FIG. 1, the tracheostomy tube can include other elements conventional in such tubes. Such elements include, for example, a cuff and an airway for inflating the cuff from, for example, a hypodermic syringe.

An entryway 48 to the secondary airway 40 couples the pneumatic vibrator 16 to the secondary airway 40. The pneumatic vibrator 16 is illustratively of the type illustrated in FIG. 5 of U.S. Pat. No. 4,586,931 and described in connection with that drawing. Such vibrators are available from Bear Medical Systems, Inc., 9335 Douglas Drive, Riverside, Calif. The switch 20 can be of any suitable type such as an electrically operated air switch or a manually operated air switch. The configuration of the compliance 18 can best be seen by referring to FIG. 2.

The compliance 18 includes a generally right circular cylindrical wall 50 and end caps 52, 54. End cap 52 is provided with connecting nipples 56, 58 on its exterior and interior, respectively. End cap 54 is provided with end caps 60, 62 on its exterior and interior, respectively. One end of length 32 of tubing engages nipple 56 to provide air to the compliance 18. Nipple 60 engages one end of length 34 of tubing to supply outlet air from the compliance 18 to the pneumatic vibrator 16. The compliance itself is provided by a resilient elastic tube 64 of balloon-like material engaging nipples 58, 62. Tube 64 can be constructed from a toy balloon or finger cot by cutting the closed end of the balloon or finger cot open and fixing the ends of the balloon or finger cot to nipples 58, 62.

Constructions of the tracheostomy tube 14 include that illustrated in FIG. 3 in which the secondary airway 40 comprises a smaller diameter tube 66 fixed, such as by gluing with an adhesive, or formed on the outer sidewall 42 of the tube 44, the interior of which forms the main airway 26 of the tracheostomy tube. A single opening 68 is formed adjacent the end 70 of tube 66 remote from the entryway 48. A stream of air containing sonic vibrations generated by pneumatic vibrator 16 under the control of switch 20 issues from opening 68 when the switch 20 is activated. These sonic vibrations flow with the air upward through the pharynx and are articulated in the same manner as his own vocal cords' natural vibrations by the patient into audibly comprehensible speech.

In the embodiment of the tracheostomy tube 114 illustrated in FIG. 4, the secondary airway 140 comprises a smaller diameter tube 166 fixed or formed on the outer sidewall 142 of the tube 144, the interior of which forms the main airway 126 of the tracheostomy tube 114. In addition to the opening 168 formed at the end 170 of tube 166 remote from the entryway 148, additional openings 172 are formed in tube 166 intermediate the entryway 148 into tube 166 and the end opening 168 remote from entryway 148.

In the embodiment of the tracheostomy tube 214 illustrated in FIG. 5, the secondary airway comprises a smaller diameter tube 266 fixed or formed on the outer sidewall 242 of the tube 244, the interior of which forms the main airway 226 of the tracheostomy tube 214. The tracheostomy tube 214 includes a tube 274 fixed or formed to the outer sidewall 242 of tube 244 at the end 270 of tube 266 remote from the entryway 248. Tube 274 extends generally transversely to the longitudinal extent of the tracheostomy tube 214 perimetrally completely around tube 244. The interior of tube 274 is in open communication with the interior of tube 266 at the junction of tubes 266, 274. A plurality of openings 272 are formed in the sidewall of tube 274 to couple sonic vibrations transported in the air stream moving from entryway 248 down tube 266 out of tube 274 into the trachea and thus upward into the pharynx of the wearer.

As previously mentioned, in addition to being fixed, such as by gluing with a suitable adhesive, to the outside of the main airway-providing tube, the secondary airway-providing tube can be formed with, or as a part of, the main airway-providing tube. This can be done, for example, by extrusion. As illustrated in FIG. 6, the secondary airway-providing tube 366 can be formed on the outer sidewall 342 of the main airway-providing tube 344. Alternatively, as illustrated in FIG. 7, the secondary airway-providing tube 466 can be formed on the inner sidewall 442 of the main airway-providing tube 444.

What is claimed is:

1. A pneumatic vibrator for providing sonic vibrations, a tracheostomy tube including means for providing a main airway, means providing a secondary airway, the secondary airway-providing means extending generally along the longitudinal extent of the tracheostomy tube for a substantial portion of its length, means providing an entryway to the secondary airway outside the entrance of the tracheostomy tube into a tracheostomy, means providing an exit from the secondary airway adjacent its end remote from the entryway, means for coupling a source of compressed air to the pneumatic vibrator, the compressed air causing vibration of the pneumatic vibrator to generate the sonic vibrations, and means for coupling the pneumatic vibrator to the entryway to supply air containing sonic vibrations thereto, the means for coupling the source of compressed air to the pneumatic vibrator comprising means providing a housing, an inlet extending through the wall of the housing to provide an inlet for compressed air into the housing, an outlet extending through the wall of the housing to provide an outlet for compressed air from the housing, and resilient elastic tubing extending between the inlet and outlet inside the housing.

2. The apparatus of claim 1 wherein the resilient elastic tubing is balloon-like.

3. The apparatus of claim 2 and further comprising means providing additional exits from the secondary airway.

4. The apparatus of claim 3 wherein the means providing additional exits from the secondary airway comprises means providing additional passageways through the wall of the secondary airway intermediate the entryway and the first-mentioned exit from the secondary airway.

5. A pneumatic vibrator for generating sonic vibrations, a tracheostomy tube comprising means for providing a main airway, means for providing a secondary airway, the secondary airway providing means extending generally along the longitudinal extent of the tracheostomy tube for a substantial portion of its length, means providing an entryway to the secondary airway outside the entrance of the tracheostomy tube into the tracheostomy, means for coupling the pneumatic vibrator to the entryway, means for providing a passageway extending generally transversely of the longitudinal extent of the tracheostomy tube generally perimetrally around the sidewall of the means providing the main airway and intersecting the means for providing the secondary airway, the transverse passageway and the means for providing the secondary airway being in open communication with each other, means providing an opening through the wall of the transverse passageway so that sonic vibrations provided to the entryway of the secondary airway are emitted from the transverse passageway through the opening through the wall of the transverse passageway, means for coupling the pneumatic vibrator to a source of compressed air including means providing a housing, an inlet extending through the wall of the housing to provide an inlet for compressed air into the housing, an outlet extending through the wall of the housing to provide an outlet for compressed air from the housing, and compliance-providing means extending within the housing between the inlet into the housing and the outlet from the housing.

6. The apparatus of claim 5 wherein the compliance providing means comprises resilient elastic tubing.

* * * * *